(12) United States Patent
Knauer et al.

(10) Patent No.: US 7,475,686 B2
(45) Date of Patent: Jan. 13, 2009

(54) EARPLUG

(75) Inventors: Richard E. Knauer, Carmel, IN (US); Alan R. Seville, Indianapolis, IN (US)

(73) Assignee: Cabot Safety Intermediate Corporation, Southbridge, MA (US)

( * ) Notice: Subject to any disclaimer, the term of this patent is extended or adjusted under 35 U.S.C. 154(b) by 456 days.

(21) Appl. No.: 10/965,939

(22) Filed: Oct. 15, 2004

(65) Prior Publication Data

US 2006/0081415 A1    Apr. 20, 2006

(51) Int. Cl.
*A61F 11/00* (2006.01)
*A61B 7/02* (2006.01)
*B29C 44/34* (2006.01)
*C08F 110/00* (2006.01)
*C08F 14/00* (2006.01)

(52) U.S. Cl. .............. 128/864; 128/865; 128/866; 128/867; 128/868; 181/135; 521/142; 521/143; 521/145

(58) Field of Classification Search ......... 128/864–868; 181/135; 521/142, 143, 145
See application file for complete search history.

(56) References Cited

U.S. PATENT DOCUMENTS

| | | | |
|---|---|---|---|
| 3,432,449 A * | 3/1969 | Deal et al. ............... 521/74 |
| RE29,487 E | 12/1977 | Gardner, Jr. | |
| 4,434,794 A | 3/1984 | Leight | |
| 4,750,669 A | 6/1988 | Leight | |
| 5,188,123 A | 2/1993 | Gardner, Jr. | |
| 5,203,352 A * | 4/1993 | Gardner, Jr. ............ 128/864 |
| 5,328,937 A * | 7/1994 | Cascino ................... 521/73 |
| 5,792,998 A | 8/1998 | Gardner et al. | |
| 6,129,175 A * | 10/2000 | Tutor et al. ............. 181/135 |
| 6,461,644 B1* | 10/2002 | Jackson et al. ......... 424/499 |
| 6,506,835 B1* | 1/2003 | Hofmann ................. 525/63 |
| 2003/0075185 A1* | 4/2003 | Ulbrich ................... 128/864 |

FOREIGN PATENT DOCUMENTS

WO    WO 02/26465 A1    4/2002

OTHER PUBLICATIONS

International Search Report for PCT/US2005/036261. Mailed Jan. 31, 2006.
Written Opinion of the International Searching Authority for PCT/US2005/036261. Mailed Jan. 31, 2006.

* cited by examiner

*Primary Examiner*—Patricia Bianco
*Assistant Examiner*—Tarla Patel
(74) *Attorney, Agent, or Firm*—Cantor Colburn LLP

(57) ABSTRACT

An earplug comprising a foam composition containing a polyvinyl chloride resin and less than about 5 wt % monomeric phthalate, based on the total weight of the foam composition, is described. The foam composition may include a plasticizer containing less than or equal to about 2 wt % monomeric phthalate, based on the total weight of the plasticizer. The earplugs have slow recovery times from 60 percent compression to 10 percent compression of about 10 to about 60 seconds.

20 Claims, 1 Drawing Sheet

EARPLUG

BACKGROUND

U.S. Pat. No. Re. 29,487 describes a roll-down type earplug comprising a slow recovery viscoelastic polymeric foam and having a size and shape adapted to be compressed, inserted into the human ear canal, and therein allowed to expand to result in an acoustic obturation of the ear canal. Such earplugs have features of easy insertability, comfort, excellent attenuation properties and their ability to be produced in a single size while competently fitting almost the entire adult population. Such an earplug is utilized by first rolling it down between thumb and fingers to the extent that it is compressed in cross section to below the size of the ear canal into which it is to be inserted. The earplug is then inserted into the ear canal and held at the inserted depth with a fingertip for enough time as to allow the polymeric foam to recover sufficiently to seat the plug within the ear canal.

One of the important features of foam compositions for such earplugs is the slow recovery time. In the case of polyvinyl chloride-based earplugs, ADMEX 523®, a polymeric phthalate based plasticizer, has typically been employed to provide the desired slow recovery properties. This plasticizer, however, contains high amounts of monomeric phthalates which may be undesirable for some applications. While these foam compositions are suitable for their intended use, there nonetheless remains a need for earplugs comprising slow recovery foam compositions.

BRIEF SUMMARY

In one aspect, an earplug comprises a foam composition, wherein the foam composition comprises a polyvinyl chloride resin and less than about 5 wt % of monomeric phthalate, based on the total weight of the foam composition.

In another aspect, an earplug comprises a foam composition, wherein the foam composition comprises about 45 wt % to about 65 wt % of a polyvinyl chloride resin; and about 30 wt % to about 50 wt % of a plasticizer, both based on the total weight of the foam composition; wherein the plasticizer comprises less than or equal to about 2 wt % of monomeric phthalate, based on the total weight of the plasticizer.

BRIEF DESCRIPTION OF THE DRAWINGS

Referring now to the drawings wherein like elements are numbered alike in several FIGURES.

Figure 1:
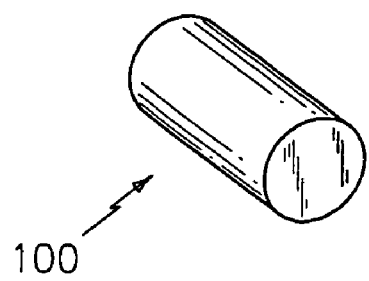
FIG. 1 shows an embodiment of a cylindrical foam earplug.

The above-described and other features will be appreciated and understood by those skilled in the art from the following detailed description, drawings, and appended claims.

DETAILED DESCRIPTION

Described herein are foam earplugs comprising a foam composition. One important property of the foam composition is the slow recovery of the foam after compression. In order to provide slow recovery properties in polyvinyl chloride foam, polymeric phthalate based plasticizers, in particular, ADMEX 523® have been employed. ADMEX 523®, however, comprises significant amounts of monomeric phthalate in addition to polymeric phthalate. Testing indicates that prior art formulations, typically containing about 42 percent by weight (wt %) ADMEX 523®, contain 8 wt % to about 10 wt % monomeric phthalate. To meet environmental limitations, it is desirable to reduce the amount of monomeric phthalate in foam compositions for foam earplugs. It has been unexpectedly discovered herein that plasticizers containing lower levels of monomeric phthalate than ADMEX 523® can be employed to produce an earplug having the desired slow recovery properties.

The foam earplugs described herein comprise a foam composition comprising a polyvinyl chloride resin and a plasticizer. The foam composition comprises less than about 5 wt % monomeric phthalate, less than or equal to about 4 wt % monomeric phthalate, less than or equal to about 2 wt % monomeric phthalate, or less than or equal to about 1 wt % monomeric phthalate, or less than or equal to about 0.5 wt % monomeric phthalate, all based on the total weight of the foam composition. One important property of the foam composition is its recovery from compression in at least one dimension, typically the width in the case of a roll-down type-foam earplug. The foam composition has a rate of recovery from 60 percent compression to 10 percent compression thereof, or 90% of its uncompressed dimension (e.g., width), of about 10 to about 60 seconds.

Suitable polyvinyl chloride resins include, for example, a homopolymer and/or a copolymer comprising greater than or equal to about 85 percent by weight of vinyl chloride and less than or equal to about 15 percent by weight of other monomers such as, for example, vinylidene chloride, vinyl esters of carboxylic acids (e.g., vinyl acetate, vinyl propionate, vinyl butyrate and vinyl benzoate), esters of unsaturated acids (e.g., alkyl acrylates such as methyl acrylate, ethyl acrylate, propyl acrylate, butyl acrylate, allyl acrylate, and the corresponding esters of methacrylic acid), vinyl aromatic compounds (e.g., styrene, ortho-chlorostyrene, para-chlorostyrene, 2,5-dichlorostyrene, 2,4-dichlorostyrene, paraethylstyrene, vinyl naphthalene, and alpha-methyl styrene), dienes (e.g., butadiene and chlorobutadiene), unsaturated amides (e.g., acrylic acid amide and acrylic acid anilide, unsaturated nitriles (e.g., acrylic acid nitrile), and esters of alpha,beta-unsaturated carboxylic acids (e.g., the methyl, ethyl, propyl, butyl, amyl, hexyl, heptyl, octyl, allyl, methallyl, and phenyl esters of maleic, crotonic and fumaric acids), and the like, and combinations comprising one or more of the foregoing monomers. Such polyvinyl chloride resins, and particularly the vinyl chloride homopolymers, can be compounded into plastisol form with a suitable plasticizer so as to result in foams having the rate of recovery and pressure characteristics necessary in the compositions from which the earplugs are fabricated. Suitable polyvinyl chloride resins include, for example, homopolymer polyvinyl chloride dispersion resins such as Colorite 1730 and Colorite 1757, commercially available from Colorite polymers.

The foam composition comprises about 45 wt % to about 65 wt % of the resin, based on the total weight of the foam composition. In one embodiment, the foam composition comprises about 50 wt % to about 60 wt % of the resin, based on the total weight of the foam composition. In another embodiment, the foam composition comprises about 52 wt % to about 57 wt % of the resin, based on the total weight of the foam composition.

The foam composition comprises a plasticizer to provide slow recovery from compression. The plasticizer comprises less than or equal to about 2 wt % of monomeric phthalate, or less than about 1 wt % of monomeric phthalate, based on the total weight of the plasticizer. A suitable plasticizer is XP6747, commercially available from Velsicol Chemical.

Optionally, a second plasticizer, such as epoxidized soybean oil, can be employed in addition so long as the overall level of monomeric phthalate remains below about 1 wt %.

The foam composition comprises about 30 wt % to about 50 wt % of the plasticizer, based on the total weight of the foam composition. In one embodiment, the foam composition comprises about 35 wt % to about 45 wt % of the plasticizer, based on the total weight of the foam composition. In another embodiment, the foam composition comprises about 35 wt % to about 38 wt % of the plasticizer, based on the total weight of the foam composition.

The foam composition optionally further comprises about 2 wt % to about 6 wt % of an epoxidized soybean oil, based on the total weight of the foam composition. In one embodiment, the foam composition comprises about 3 wt % to about 5 wt % of the epoxidized soybean oil, based on the total weight of the foam composition. In another embodiment, the foam composition comprises about 3.5 wt % to about 4 wt % of the epoxidized soybean oil, based on the total weight of the foam composition. The epoxidized soybean oil may serve one or several purposes in the foam composition. One purpose is to act as a heat stabilizer against degradation of the polyvinyl chloride. A second purpose is to plasticizer the foam composition. Suitable epoxidized soybean oils include, for example, Flexol ESO, Drapex 6.8 from Crompton, and Paraplex G62 from Rhom and Haas.

The foam composition comprises a chemical foaming agent (also known as a blowing agent) such as for example azodicarbonamide, commercially available as Celogen® AZ 150 from Crompton. The chemical foaming agent produces the foaming action for the polyvinyl chloride composition to produce a foam. Azodicarbonamide, when heated, decomposes primarily into nitrogen, carbon dioxide and carbon monoxide. These generated gases can produce the foaming action of the polyvinyl chloride composition. Other chemical foaming agents which may be employed include, for example, diazoaminobenzene, azobis(isobutyronitrile), benzenesulfonylhydrazide, p-toluenesulfonylhydrazide, and combinations comprising one or more of the foregoing chemical foaming agents.

The foam composition may comprise about 3 wt % to about 5 wt % of the chemical foaming agent, based on the total weight of the foam composition. In one embodiment, the foam composition comprises about 3.5 wt % to about 4.5 wt % of the chemical foaming agent, based on the total weight of the foam composition. In another embodiment, the foam composition comprises about 3.7 wt % to about 4.2 wt % of the chemical foaming agent, based on the total weight of the foam composition.

The foam composition optionally further comprises a resin stabilizer. The resin stabilizer can inhibit decomposition of the polymeric resin that may occur at processing temperatures. In addition, the resin stabilizer can further catalyze the decomposition of the chemical blowing agent. A suitable resin stabilizer for polyvinyl chloride is a blend of an organic zinc carboxylate and a phosphite chelating agent, commercially available as Vanstay 8960 from R.T. Vanderbilt Co. Inc.

The foam composition may comprise about 1 wt % to about 3 wt % of the resin stabilizer, based on the total weight of the foam composition. In one embodiment, the foam composition comprises about 1.5 wt % to about 2.5 wt % of the resin stabilizer, based on the total weight of the foam composition. In another embodiment, the foam composition comprises about 1.7 wt % to about 2.2 wt % of the resin stabilizer, based on the total weight of the foam composition.

The foam composition optionally further comprises a cell stabilizer such as Product VS 103 from Air Products. The cell stabilizer can be a solution of mineral spirits and polybutyl methracrylate. In the composition, the stabilizer may act as a surfactant in that it strengthens the walls of the cells so that they do not rupture during the foaming process, allowing a fine cell foam to be produced. The foam composition may comprise about 0.3 wt % to about 3.0 wt % of the cell stabilizer, based on the total weight of the foam composition. In one embodiment, the foam composition comprises about 0.5 wt % to about 1.5 wt % of the cell stabilizer, based on the total weight of the foam composition. In another embodiment, the foam composition comprises about 0.8 wt % to about 1.1 wt % of the cell stabilizer, based on the total weight of the foam composition.

With respect to the characteristics of the foam composition, the slow recovery rate in returning from 60 percent compression to 10 percent compression of the foam composition confers to the user the ability to initially compress or otherwise deform the earplug and provide sufficient time for insertion thereof into the ear canal. Subsequent to insertion, the compressed or deformed earplug slowly recovers and attempts to regain its original shape. By so doing, the recovering foam composition conforms to the structure of the ear canal and establishes substantially complete obturation thereof. In one embodiment, the recovery rate from 60 percent compression to 10 percent compression of the foamed polymer composition will be about 10 to about 60 seconds, or about 15 and about 40 seconds.

Figure 2:
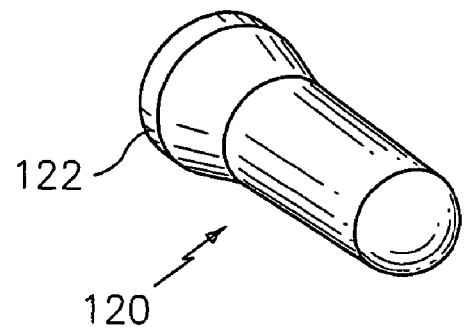
FIG. 2 is a view of a cylindrical earplug with a flared end.

Referring now to FIGS. 1-2, exemplary earplugs are shown. Earplug shapes are well known in the art. One shape is a cylindrical foam earplug 100 as shown in FIG. 1. Another embodiment is a cylindrical shape 120 with flared end 122 as shown in FIG. 2. Cylindrical earplugs such as those illustrated in FIG. 1 are roll-down plugs that can be compressed, inserted into the ear canal, and allowed to expand to result in comfortable and complete obturation of the ear canal.

Figure 3:
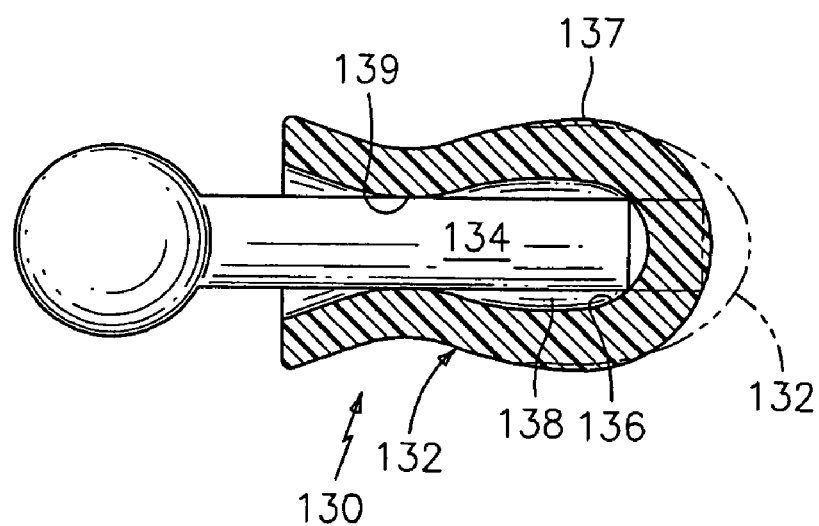
FIG. 3 is a view of an embodiment of an earplug having a hollow body and a stem.

FIG. 3 illustrates an earplug 130 which includes a hollow body or shell 132 and a stem 134 which lies within the cavity 136 of the shell. The largest diameter portion of the shell 137 can contract in diameter to fit into the ear canal. The shell cavity 136 may have a larger diameter than the stem 134 immediately within the shell to provide a gap 138 that permits reduction of the shell diameter. In order to prevent accidental loss of the stem 134, there may be a slight interference between the stem 134 and the walls of a throat 139 formed in the cavity 136. The shell 132 is constructed of a foam composition, by a processes such as, for example, dip molding. The stem 134 may be constructed of an elastomeric material which is stiffer than the material of the shell 132 but which can bend. The earplug can be utilized by pressing it into the ear canal.

Other embodiments include a slippery outer surface on the earplug, thereby aiding the earplug device to slide by the ear canal, and an embossed surface on the earplug.

In one embodiment, the foam earplug may be punched or bored from a sheet of polymeric foam. A sheet of polyvinyl chloride foam may be formed by, for example, combining the polyvinyl chloride resin and the plasticizer to form a liquid plastisol composition, casting the plastisol with a knife over roll or reverse roll coater onto release paper, and heating the plastisol at about 180° C. to about 220° C. to create a foam. The foam sheet may be rolled and then cut with a die press. The die may have a cylindrical shape or another suitable shape such as, for example, hexagonal.

In another embodiment, such as that illustrated in FIG. 3, the body or shell of the earplug may be formed by dip molding. In a dip molding process, a heated mandrel in that shape of the earplug body or shell is dipped into a liquid plastisol comprising the resin and the plasticizer. The mandrel may be heated to a temperature of about 140° C. to about 200° C. The heated mandrel may be allowed to remain in the plastisol for a time sufficient for the plastisol to partially gel on the mandrel to a thickness of about 0.01 to about 0.05 inches. The mandrel is then withdrawn from the plastisol so as to minimize dripping and running of the plastisol which could form an imperfect outer surface which would not fuse at a uniform rate. The plastisol on the mandrel then is fully cured at a temperature of about 350° F. to about 450° F. for about 100 to about 400 seconds. The mandrel may then be cooled in air or water and the finished part stripped from the mandrel for storage or packing. The foam earplug may be encapsulated or further coated if desired, or embossed. The foam earplug may also be crushed to rupture some of the closed cells to allow at least some air flow. Crushing may prevent puckering, or softens the foam to allow ease of compression.

The recovery properties of the foam composition can be tested as follows. Plugs of the foam composition are cut with a hollow tube borer, the dimensions of the plugs of about 0.530 to about 0.560 inch in diameter and having a length of about 0.650 to about 0.775 inch. The plug is twirled between the thumb and forefinger for a period of 1 minute while slowly compressing it. The plug is compressed 60% or to about 40% of its uncompressed diameter in the first 30 seconds and maintained at that diameter for the remaining 30 seconds. The plug is then dropped into a clear glass or acrylic tube having an internal diameter of about 0.49 inches or about 90% of the diameter of the uncompressed plug. The tube is then held vertically with one end near a hard surface. The tube is gently tapped on the surface until it will pick up the plug due to the plug's expansion and contact with the inside of the tube. The time from the time is released until the tube will pick it up is the recovery of the plug.

The ability of the plug to block sound in an ear canal is measured in accordance with ANSI S3.19-1974 Method for the Measurement of Real-Ear Protection of Hearing Protectors and Physical Attenuation of Earmuffs. In this test, Real-Ear Attenuation at Threshold (REAT) testing is conducted in a laboratory test chamber which is a semi-reverberant, double-walled, structurally isolated room using third-octave bands of noise as test signals. A human subject responds to the test signals at her/his threshold, i.e., as soon as the subject can detect the signals, in both Open (nothing in or around the ears) and Occluded (hearing protector in the ears) conditions. The difference in sound pressure level (SPL) between the two conditions is the attenuation afforded by the Hearing Protector. This difference is recorded in decibels of attenuation provided by the hearing protector at a given frequency.

The invention is further illustrated by the following non-limiting example.

EXAMPLE

TABLE 1

| Component | Wt % of total weight of composition |
|---|---|
| Colorite PVC | 52.83 wt % |
| XP6747 Plasticizer | 36.75 wt % |
| Flexol Epoxidized Soybean Oil | 3.45 wt % |
| Celogen AZ150 | 3.77 wt % |
| Vanstay 8960 | 1.84 wt % |
| VS-103 | 0.92 wt % |
| Harwick HCC29445 Yellow | 0.44 wt % |

The above materials were mixed together in a 500 gallon cone screw mixer, producing approximately 4500 pounds of a plastisol. The materials were added in such an order as to maintain a high, but constant mixing torque to ensure proper dispersion of the raw materials. Immediately following mixing, the plastisol was degassed in a continuous rotary drum degasser and stored in containers to cool. The plastisol was then cast onto release paper in a continuous casting process. The plastisol was spread to an even gage over the release paper using a knife over roll coater. The coated release paper was then heated in a continuous casting oven for approximately 7 minutes at a temperature of approximately 400° F. and allowed to cool. The cooled material was stored for approximately 1 month to allow the foam properties to stabilizer. Following the aging period, the foam was die cut into the foam earplug by means of the punch type die. The properties were measured after allowing sufficient time for the punched plugs to expand to their original height and equilibrate under standard conditions.

The concentration of various monomeric phthalates in the foam composition was analyzed by gas chromatography-mass spectrometry. The results are given in Table 2.

TABLE 2

| Monomeric phthalate | Wt % based on total weight of foam composition |
|---|---|
| Dimethylphthalate | 0.054 |
| Diethylphthalate | <0.001 |
| Di-n-butylphthalate | <0.001 |
| Butyl,Benzylphthalate | 0.0028 |
| Bis(2-Ethylhexyl)phthalate | 0.09 |
| Dioctylphthalate | 0.019 |
| Diisononylphthalate | 0.04 |
| Diisooctylphthalate | 0.1 |

The properties of the foam earplugs formed as in Table 1 are reported below.

TABLE 3

| Properties | |
|---|---|
| Foam density | 5.91 lb/ft$^3$ |
| Recovery from 60% compression to 10% compression | 31 seconds |

| ANSI S3.19-1974 attenuation test. Five subject average Frequency | Attenuation |
|---|---|
| 125 Hz | 27.8 db |
| 250 Hz | 35.5 db |
| 500 Hz | 44.7 db |
| 1000 Hz | 42.0 db |
| 2000 Hz | 35.8 db |
| 3150 Hz | 41.0 db |
| 4000 Hz | 42.7 db |
| 6300 Hz | 46.2 db |
| 8000 Hz | 45.1 db |

Thus, the earplugs containing low monomeric phthalate have a recovery from 60% compression to 10% compression of 31 seconds, well within the acceptable range. Also, the results of the attenuation test show that the level of attenuation is suitable for foam earplugs. The attenuation is comparable to that for prior art foam earplugs made using ADMEX 523® as a plasticizer.

The terms "first," "second," and the like, herein do not denote any order, quantity, or importance, but rather are used to distinguish one element from another, and the terms "a" and "an" herein do not denote a limitation of quantity, but rather denote the presence of at least one of the referenced item. The term "cylindrical" as employed herein includes within its scope structures having a relatively shallow truncated cone shape, a substantially spherical shape, and shapes intermediate to a truncated cone and a spherical shape.

All ranges disclosed herein are inclusive and combinable. While the invention has been described with reference to a preferred embodiment, it will be understood by those skilled in the art that various changes may be made and equivalents may be substituted for elements thereof without departing from the scope of the invention. In addition, many modifications may be made to adapt a particular situation or material to the teachings of the invention without departing from essential scope thereof. Therefore, it is intended that the invention not be limited to the particular embodiment disclosed as the best mode contemplated for carrying out this invention, but that the invention will include all embodiments falling within the scope of the appended claims.

All cited patents, patent applications, and other references are incorporated herein by reference in their entirety.

The invention claimed is:

1. An earplug comprising a foam composition, wherein the foam composition consists essentially of about 45 wt % to about 65 wt % of a polyvinyl chloride resins, about 30 wt % to about 50 wt % of a plasticizer, and less than about 5 wt % of monomeric phthalate plasticizer, based on the total weight of the foam composition.

2. The earplug of claim 1, wherein the foam composition consists essentially of about 45 wt % to about 65 wt % of a polyvinyl chloride resin, about 30 wt % to about 50 wt % of a plasticizer, and less than or equal to about 4 wt % of monomeric phthalate plasticizer, based on the total weight of the foam composition.

3. The earplug of claim 1, wherein the foam composition consists essentially of about 45 wt % to about 65 wt % of a polyvinyl chloride resin, about 30 wt % to about 50 wt % of a plasticizer, and less than or equal to about 1 wt % of monomeric phthalate plasticizer, based on the total weight of the foam composition.

4. The earplug of claim 1, wherein the foam composition consists essentially of about 45 wt % to about 65 wt % of a polyvinyl chloride resin, about 30 wt % to about 50 wt % of a plasticizer, and less than or equal to about 0.5 wt % of monomeric phthalate plasticizer, based on the total weight of the foam composition.

5. The earplug of claim 1, wherein the foam composition has a rate of recovery from 60 percent compression to 10 percent compression of about 10 to about 60 seconds.

6. The earplug of claim 1, wherein the foam composition has a rate of recovery from 60 percent compression to 10 percent compression of about 15 to about 40 seconds.

7. The earplug of claim 1, wherein the foam composition comprises a plasticizer comprising less than or equal to about 2 wt % monomeric phthalate plasticizer, based on the total weight of the plasticizer.

8. The earplug of claim 1, wherein the foam composition further comprises epoxidized soybean oil.

9. The earplug of claim 1, wherein the foam composition further comprises a chemical foaming agent, a resin stabilizer, a cell stabilizer, or a combination of one or more of the foregoing additives.

10. The earplug of claim 1, wherein the plasticizer is a polymeric phthalate plasticizer.

11. An earplug comprising a foam composition, wherein the foam composition consists essentially of:
   about 45 wt % to about 65 wt % of a polyvinyl chloride resin; and
   about 30 wt % to about 50 wt % of a plasticizer, both based on the total weight of the foam composition, wherein the plasticizer comprises less than or equal to about 2 wt % monomeric phthalate plasticizer, based on the total weight of the plasticizer.

12. The earplug of claim 11, wherein the plasticizer comprises less than or equal to about 1 wt % monomeric phthalate plasticizer, based on the total weight of the plasticizer.

13. The earplug of claim 11, wherein the foam composition comprises less than or equal to about 1 wt % of monomeric phthalate plasticizer, based on the total weight of the foam composition.

14. The earplug of claim 11, wherein the foam composition comprises less than or equal to about 0.5 wt % of monomeric phthalate plasticizer, based on the total weight of the foam composition.

15. The earplug of claim 11, wherein the foam composition further comprises epoxidized soybean oil.

16. The earplug of claim 11, wherein the foam composition further comprises a chemical foaming agent, a resin stabilizer, a cell stabilizer, or a combination of one or more of the foregoing additives.

17. The earplug of claim 11, wherein the foam composition has a rate of recovery from 60 percent compression to 10 percent compression of about 10 to about 60 seconds.

18. The earplug of claim 11, wherein the foam composition has a rate of recovery from 60 percent compression to 10 percent compression of about 15 to about 40 seconds.

19. The earplug of claim 11, wherein the plasticizer is a polymeric phthalate plasticizer.

20. An earplug comprising a foam composition, wherein the foam composition consists essentially of:
   45 wt % to 65 wt % of a polyvinyl chloride resin; and
   30 wt % to 50 wt % of a plasticizer, both based on the total weight of the foam composition, wherein the plasticizer comprises less than or equal to 2 wt % monomeric phthalate plasticizer, based on the total weight of the plasticizer.

* * * * *

UNITED STATES PATENT AND TRADEMARK OFFICE
CERTIFICATE OF CORRECTION

PATENT NO. : 7,475,686 B2  Page 1 of 1
APPLICATION NO. : 10/965939
DATED : January 13, 2009
INVENTOR(S) : Richard E. Knauer It is certified that error appears in the above-identified patent and that said Letters Patent is hereby corrected as shown below:

<u>Column 7</u>
Line 21, claim 1, delete "resins," and insert -- resin, -- therefore.

Signed and Sealed this

Twelfth Day of May, 2009

JOHN DOLL
*Acting Director of the United States Patent and Trademark Office*